(12) United States Patent
Jonnalagadda et al.

(10) Patent No.: US 6,350,465 B1
(45) Date of Patent: Feb. 26, 2002

(54) HEADACHE TREATMENT AND METHOD

(76) Inventors: Murali M. R. Jonnalagadda; Venkata Thirumala Devi-Jonnalagadda, both of 104 Peachtree Dr., Jacksonville, NC (US) 28546

( * ) Notice: Subject to any disclaimer, the term of this patent is extended or adjusted under 35 U.S.C. 154(b) by 0 days.

(21) Appl. No.: 09/764,608

(22) Filed: Jan. 17, 2001

(51) Int. Cl.$^7$ .......................... A61P 25/06; A61P 23/02; A61M 31/00; A61M 19/00
(52) U.S. Cl. ................ 424/434; 514/817; 514/818; 604/514
(58) Field of Search ................ 514/816, 817, 514/818; 424/434

(56) References Cited

U.S. PATENT DOCUMENTS 5,008,289 A * 4/1991 Bernstein .................. 514/535

* cited by examiner

*Primary Examiner*—Edward J. Webman
*Assistant Examiner*—Helen Nguyen
(74) *Attorney, Agent, or Firm*—Coats & Bennett, P.L.L.C.

(57) ABSTRACT

A method of treating headaches by blocking the sphenopalatine ganglion comprises using a first device to anesthetize a front portion of the nasal cavity. A second device is used to anesthetize a rear portion of the nasal cavity. After these priming anesthetizations, a primary pain medication delivery device is used to discharge an anesthetic to the sphenopalatine ganglion to treat the headache.

13 Claims, 5 Drawing Sheets

HEADACHE TREATMENT AND METHOD

FIELD OF THE INVENTION

The present invention relates to a set of devices and a technique for treating headaches and particularly migraines.

DESCRIPTION OF THE RELATED ART

Severe headaches are suffered by large numbers of the American population. It is estimated that 1 in 10 males and 1 in 4 females experience debilitating headaches regularly. Even larger percentages may experience the occasional mild headache capable of being treated with an over the counter analgesic, such as aspirin, ibuprofen, or acetaminophen. Severe headaches may substantially incapacitate the individual suffering from the headache. Such incapacitation may lead to losses in productivity, inability to work, and a general deterioration of quality of life.

There are presently two techniques by which severe headaches are treated with a sphenopalatine ganglion block. Both of these techniques involve treatment by a medical provider in an office or hospital setting. The first technique comprises using a rigid cotton swab coated with a pain medication. The cotton swab is inserted through the nasal passage to the sphenopalatine ganglion. The cotton tip then swabs the area near the ganglion to introduce the pain medication thereto. The rigid swab may cause trauma to the nasal cavity and cause other discomfort to the individual enduring the treatment.

The second technique comprises tilting the head of the headache sufferer backwards and using a syringe to trickle a pain medication through the nasal cavity to the ganglion in question.

As both of these techniques require the supervision of a medical provider, they are expensive. While some of this tab may be paid for by insurance providers or Medicare, it is still inconvenient for the individual to travel to the medical provider's office to receive the treatment.

Thus, a method of providing an effective pain medication regimen for severe headaches that does not require the supervision of a medical provider is needed.

BRIEF SUMMARY OF THE INVENTION

The present invention comprises a series of three devices, which progressively anesthetize the nasal cavity and the sphenopalatine ganglion. In particular, a first device comprises a compressible bulb having a flexible nozzle attached thereto. The flexible nozzle may be approximately 1.5 inches (3.75 cm) long. The compressible bulb is filled with an over the counter anesthetic. The individual suffering from the headache or a trusted companion may insert the flexible nozzle into the headache sufferer's nostril and squeeze the compressible bulb. This discharges the anesthetic into the nasal cavity. The mucous membrane rapidly absorbs the anesthetic, thereby priming the nasal cavity for the insertion of the second device.

The second device comprises a compressible bulb with a longer flexible nozzle. In particular, the flexible nozzle may be approximately three inches (7.5 cm) long. The compressible bulb of the second device is likewise filled with an anesthetic. The second device is inserted into the nostril of the headache sufferer and the compressible bulb compressed. This discharges the anesthetic into the nasal cavity at a point beyond the initial insertion of the first device. Again, the mucous membrane rapidly absorbs the anesthetic thereby priming the nasal cavity for the insertion of the final device.

The final device comprises a syringe having a long flexible nozzle with a wicking material disposed therein. An anesthetic is placed into the syringe and saturates the wicking material. The terminal end of the flexible nozzle has some portion of the wicking material exposed. The final device is then inserted into the nasal cavity through the nostril until the wicking material abuts or is proximate to the sphenopalatine ganglion. A guard is removed from the syringe, and the plunger of the syringe is depressed. This forces the anesthetic through the wicking material, resulting in a discharge onto the ganglion.

DETAILED DESCRIPTION OF THE INVENTION

The present invention comprises three devices which when used properly together provide an effective headache treatment method. An overview of the structures associated herewith will be presented so that the discussion of the method is facilitated.

Figure 1:
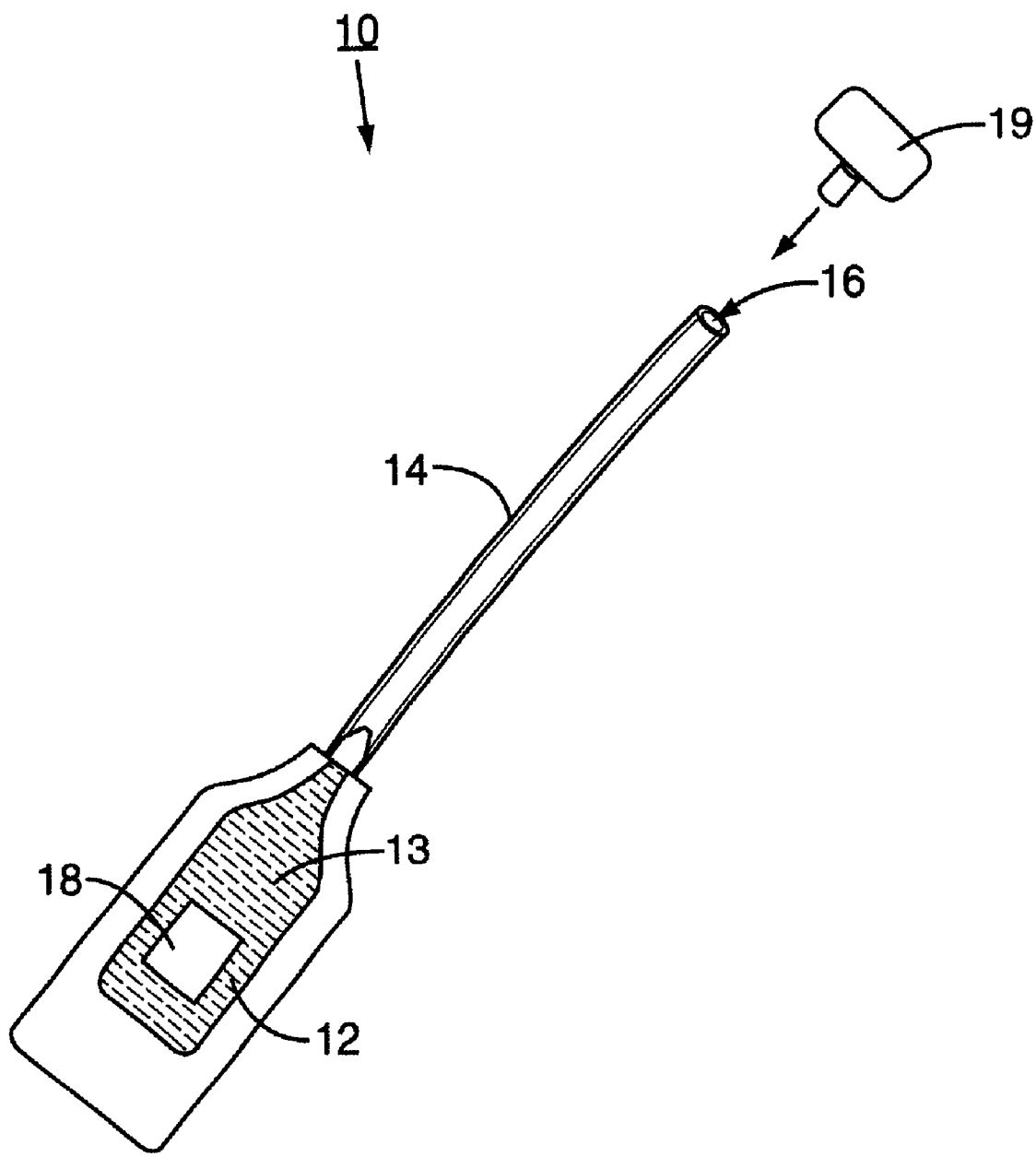
FIG. 1 illustrates a front perspective view of a first device used in the present invention.

FIG. 1 illustrates a first priming device 10 comprising a reservoir or compressible bulb 12 filled with a fluid 13 and having a flexible nozzle 14 approximately 1.5 inches long (3.75 cm). Nozzle 14 may include an aperture 16 capable of being capped by cap 19. Compressible bulb 12 may further comprise a label 18 indicating the nature of the fluid 13 to comply with appropriate statutes or regulations. Fluid 13 may comprise an anesthetic such as benzocaine. Cap 19 is selectively removable as is well understood. Compression of the compressible bulb 12 results in the discharge of fluid 13 through the flexible nozzle 14 and specifically through aperture 16. Flexible nozzle 14 may be made from any number of materials capable of surviving conventional sterilization techniques without losing its flexibility. One appropriate material would be a clear vinyl.

Figure 2:
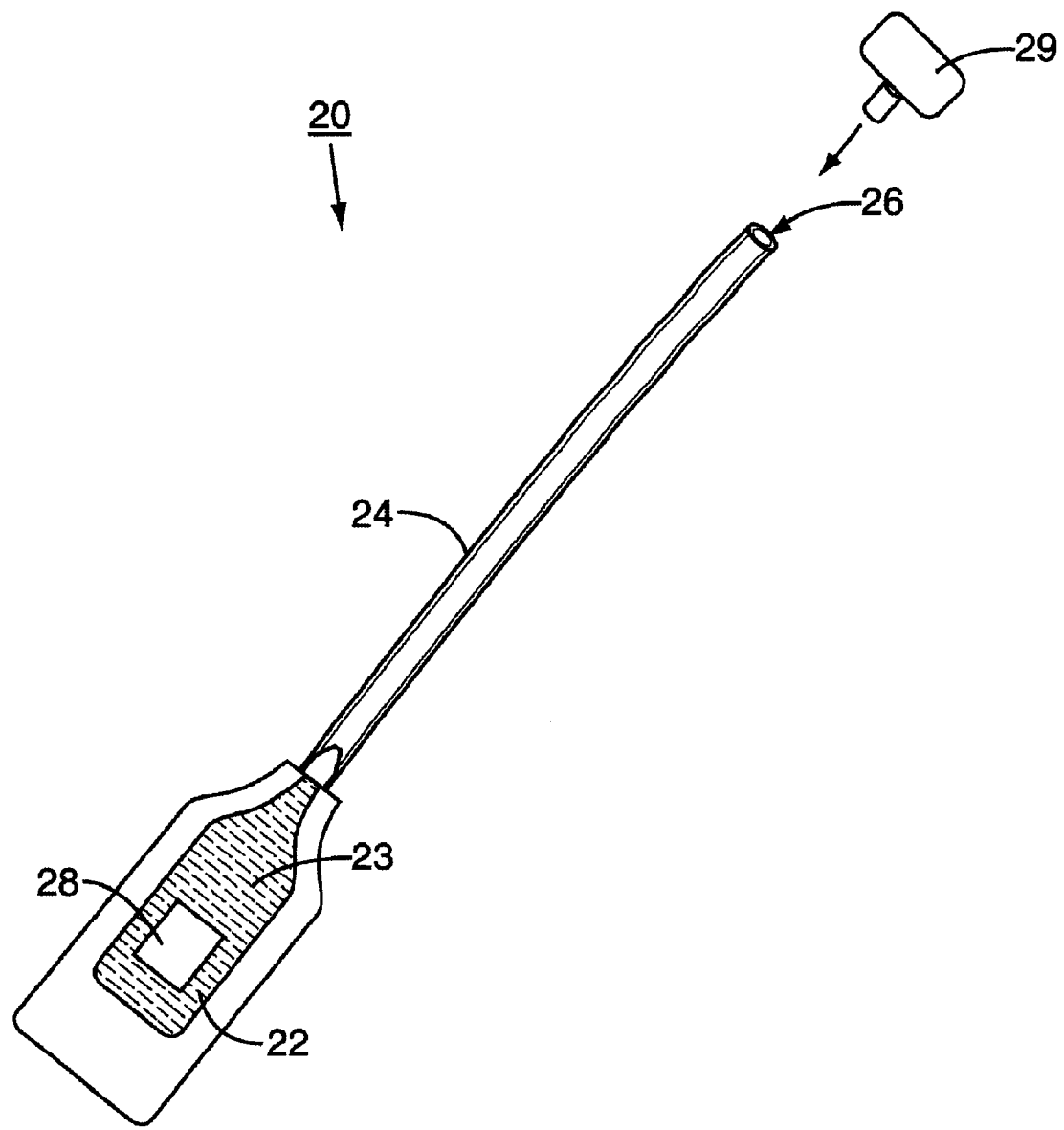
FIG. 2 illustrates a front perspective view of a second device used in the present invention.

FIG. 2 illustrates a second priming device 20 comprising a reservoir or compressible bulb 22 filled with a fluid 23 and having a flexible nozzle 24 approximately three inches long (7.5 cm). Flexible nozzle 24 may include an aperture 26 capable of being capped by cap 29. Compressible bulb 22 may further comprise a label 28 indicating the nature of the fluid 23 to comply with appropriate statutes or regulations. Fluid 23 may comprise an anesthetic such as benzocaine. Cap 29 is selectively removable as is well understood. Compression of the compressible bulb 22 results in the discharge of fluid 23 through the nozzle 24 and specifically through aperture 26. Flexible nozzle 24 may likewise be made from any number of materials capable of surviving conventional sterilization techniques without losing its flexibility.

Figure 3:
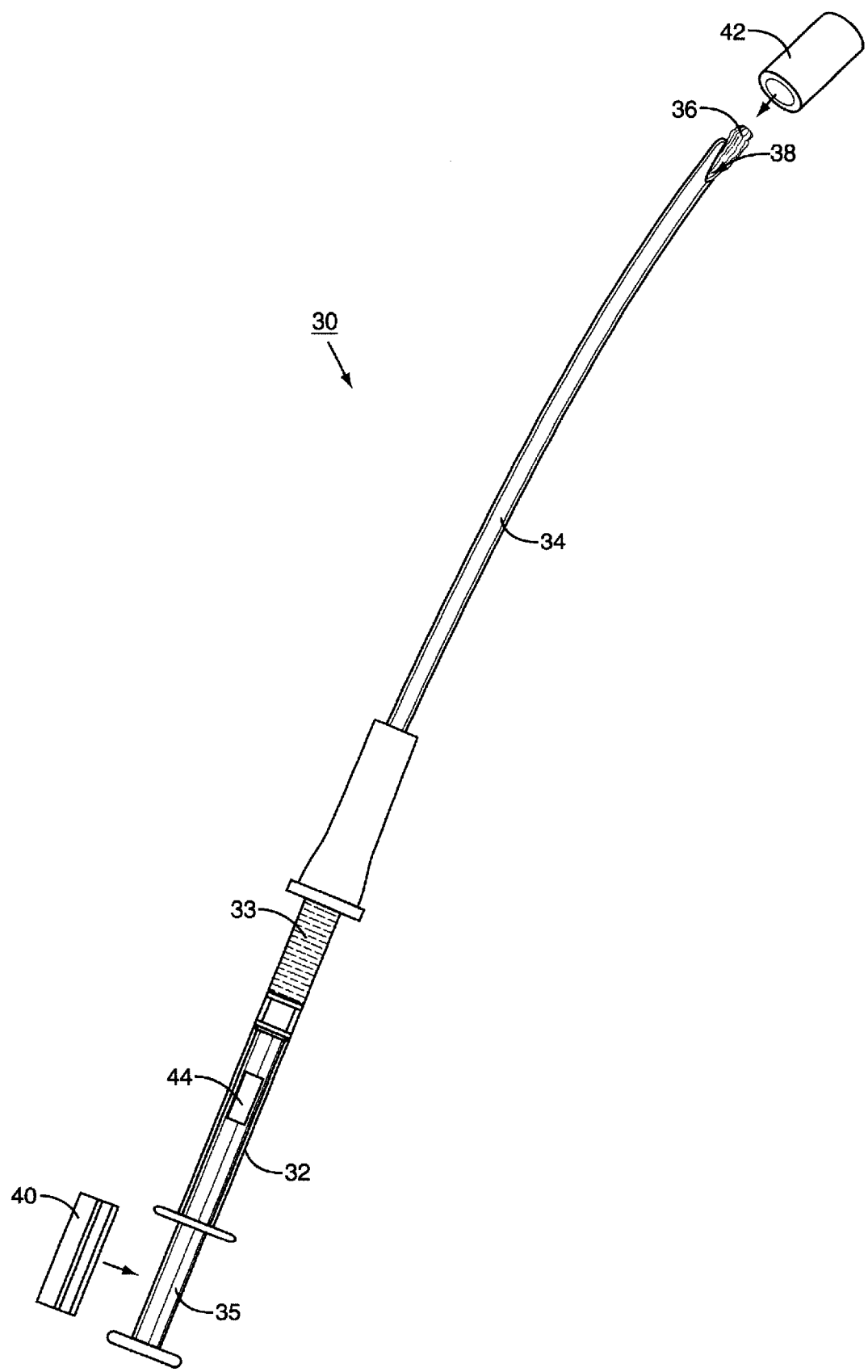
FIG. 3 illustrates a front perspective view of a final device used in the present invention.

FIG. 3 illustrates a pain medication delivery device 30 that comprises a syringe 32 attached to a flexible nozzle 34. Syringe 32 further comprises a plunger 35. Syringe 32 contains a fluid 33 therein. Fluid 33 may be benzocaine, a fluid headache treatment pain medication. A wicking material 36 such as cotton, or polyester blended cotton, or the like may be contained within the flexible nozzle 34 and extend from aperture 38. A syringe guard 40 prevents inadvertent depression of plunger 35 and is selectively removable as is well understood. A cap 42 is further selectively placed over the terminal end of the nozzle 34 and wicking 36. A label 44 may be positioned on the syringe 32 detailing the fluid 33 to comply with the appropriate statutes and regulations.

Figure 4:
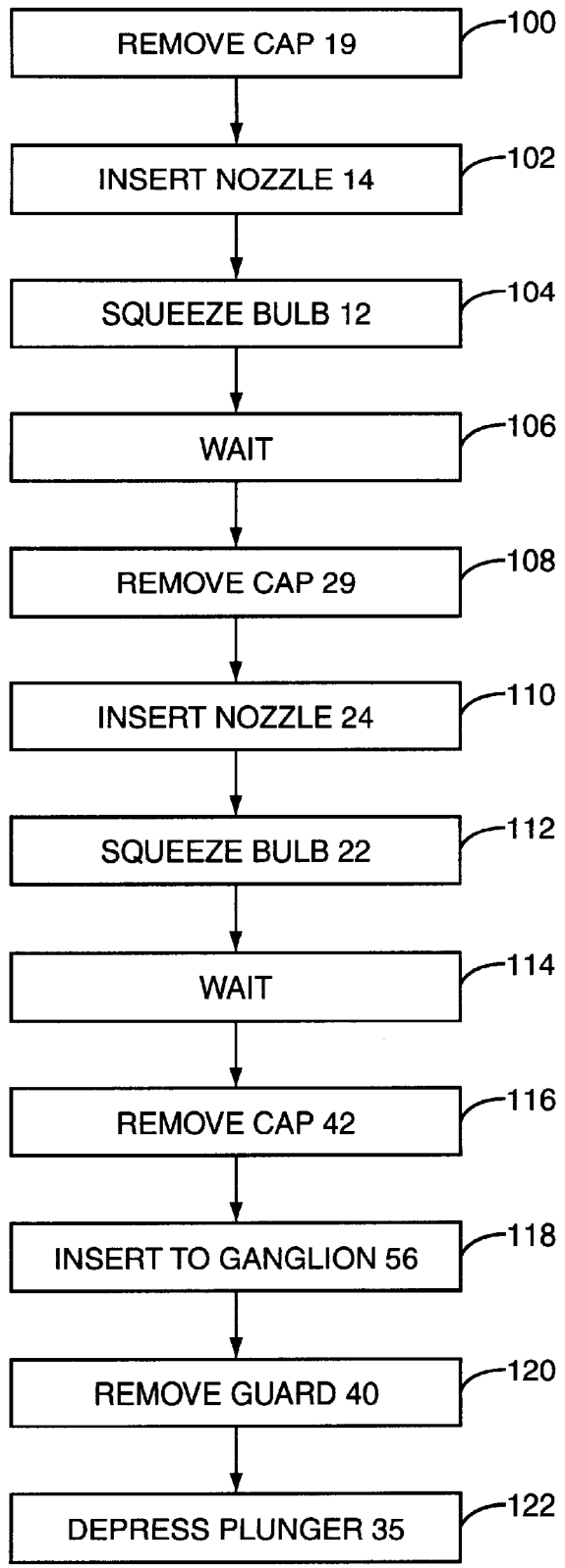
FIG. 4 illustrates a flow chart diagram of the steps of one embodiment of the present invention.
Figure 5:
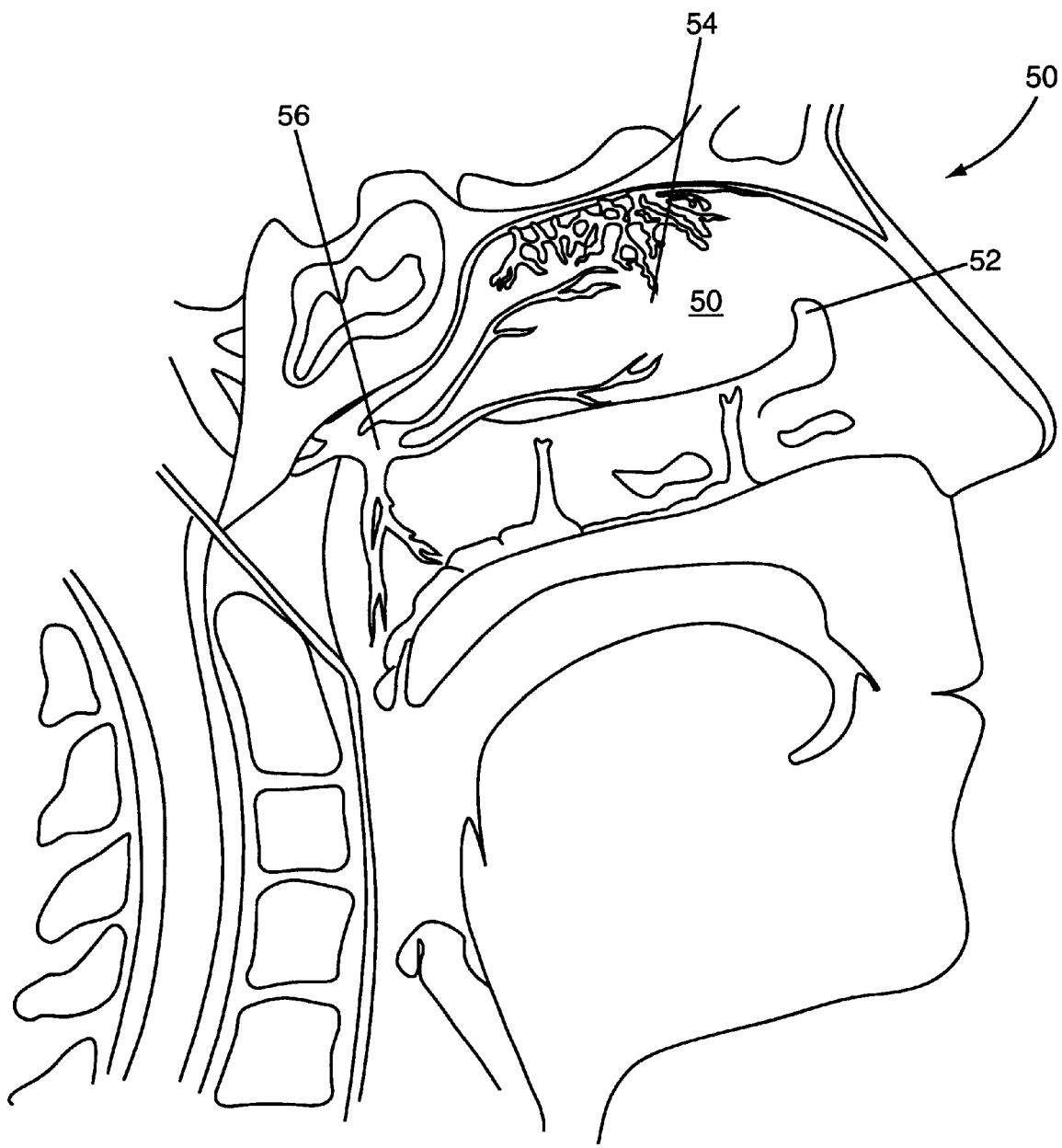
FIG. 5 illustrates a cross sectional view of a human head.

With that discussion of the three delivery devices 10, 20, and 30, the present methodology may now be explicated with reference to FIG. 4. Upon the realization that an individual is suffering from a severe headache, the individual or a trusted companion may remove cap 19 from the first priming device 10 (block 100). The flexible nozzle 14 is then inserted into the nasal cavity 50 (FIG. 5) to a first insertion point 52 (block 102). The compressible bulb 12 is then compressed thereby discharging fluid 13 from bulb 12 through nozzle 14 and specifically through aperture 16 into the nasal cavity 50 (block 104). An appropriate amount of time passes for the anesthetic within fluid 13 to take effect to numb the nasal cavity 50 (block 106). The cap 29 is then removed from the second priming device 20 (block 108). The flexible nozzle 24 is then inserted in the nasal cavity 50 to the second insertion point 54 (block 110). The compressible bulb 22 is then compressed, thereby discharging fluid 23 through nozzle 24 and out aperture 26 into the nasal cavity 50 (block 112). Again an appropriate amount of time passes for the anesthetic within fluid 23 to take effect (block 114). Having primed both an outer portion of the nasal cavity 50 with the first fluid 13 and the inner portion of the nasal cavity 50 with the second fluid 23, the final pain medication may then be provided. The cap 42 is removed (block 116). The flexible nozzle 34 is then inserted to the nasal cavity 50 to the sphenopalatine ganglion 56 such that the wicking 36 is proximate to the ganglion 56 (block 118). The syringe guard 40 is then removed (block 120). Note that the syringe guard 40 may be removed prior to insertion if desired. After proper insertion, the plunger 35 is depressed (block 122) thereby discharging the fluid 33 through the nozzle 34 and out aperture 38. This introduces the anesthetic within fluid 33 to the sphenopalatine ganglion 56 for treatment of the severe headache.

As the pain medication described herein is available over the counter, it is expected that the present methodology would not require a visit to the office of a medical care provider. Further, with proper instruction, an individual may perform this technique upon themselves, or with the assistance of a trusted companion. The flexible nature of the nozzles 14, 24, and 34 allow insertion into the nasal cavity 50 without risk of trauma thereto. The preliminary anesthetizing of the nasal cavity 50 with the first priming device 10 and a second priming device 20 further reduces the likelihood of trauma to the nasal cavity. This specifically avoids the need for a rigid swab being inserted into the nasal cavity with the attendant risks of trauma associated therewith while at the same time providing introduction of the pain medication in close proximity to the sphenopalatine ganglion 56, which is not presently achieved through the syringe trickle method.

While using both priming devices 10 and 20 may be desirable to the extent that it allows the nasal cavity 50 to be progressively anesthetized, it is possible that only a single priming step if performed with a single priming device having a flexible nozzle. Likewise, while the wicking 36 cushions the mucous membrane as the flexible nozzle 34 abuts the ganglion 56, the wicking 36 does not have to be used.

It should be appreciated that the dimensions provided herein are contemplated as being designed for an adult. A child sized version may likewise be created which is correspondingly smaller. Other sizes may also be appropriate for the vertically challenged or particularly large individuals such as basketball players and the like.

Note further that the caps 19, 29, and 42 are designed to remain in place, keeping the terminal ends of the respective nozzles 14, 24, and 34 clean and preventing discharge therefrom until desired. The particular shape is not material to the present invention.

The present invention may, of course, be carried out in other specific ways than those herein set forth without departing from the scope and the essential characteristics of the invention. The present embodiments are therefore to be construed in all aspects as illustrative and not restrictive and all changes coming within the meaning and equivalency range of the appended claims are intended to be embraced therein.

What is claimed is:

1. A method of treating a headache, comprising:
    inserting a nozzle on a first priming device into the nasal cavity of the headache sufferer;
    discharging a priming anesthetic through said nozzle into the nasal cavity of the headache sufferer;
    inserting a nozzle on a pain medication delivery device to a point proximate the sphenopalatine ganglion of the headache sufferer; and
    discharging a primary anesthetic through the pain medication delivery device's nozzle proximate the sphenopalatine ganglion.

2. The method of claim 1 further comprising removing the nozzle of the first priming device prior to insertion of the nozzle on the pain medication delivery device.

3. The method of claim 1 further comprising:
    inserting a nozzle on a second priming device into the nasal cavity of the headache sufferer to a point past the first insertion point; and
    discharging a second priming anesthetic through said nozzle into the nasal cavity of the headache sufferer.

4. The method of claim 1 wherein inserting a nozzle on a first priming device comprises inserting a flexible nozzle to a point approximately 1.5 inches into the nasal cavity.

5. The method of claim 3 wherein inserting a nozzle on a second priming device comprises inserting a flexible nozzle to a point approximately 3 inches into the nasal cavity.

6. The method of claim 1 wherein discharging a primary anesthetic through the pain medication delivery device's nozzle comprises discharging a primary anesthetic through a wicking material disposed in the pain medication delivery device's nozzle.

7. The method of claim 1 wherein discharging a primary anesthetic through the pain medication delivery device's nozzle comprises depressing a plunger in a syringe.

8. The method of claim 1 wherein discharging a priming anesthetic through said nozzle into the nasal cavity of the headache sufferer comprises compressing a compressible bulb.

9. A method of treating a headache comprising:
    inserting a first flexible nozzle attached to a first compressible bulb into the nasal cavity of the headache sufferer;
    compressing the first compressible bulb to discharge a first priming anesthetic into the nasal cavity of the headache sufferer;

inserting a second flexible nozzle attached to a second compressible bulb into the nasal cavity of the headache sufferer to a point her within the nasal cavity than the first flexible nozzle;

compressing the second compressible bulb to discharge a second priming anesthetic into the nasal cavity of the headache sufferer;

inserting a third flexible nozzle attached to a syringe into the nasal cavity of the headache sufferer to a point proximate the sphenopalatine ganglion; and depressing a plunger on the syringe to discharge a primary anesthetic at a point proximate the sphenopalatine ganglion to treat the headache.

10. The method of claim 9 further comprising removing a cap from said first flexible nozzle prior to insertion.

11. The method of claim 9 wherein depressing a plunger on the syringe to discharge a primary anesthetic at a point proximate the sphenopalatine ganglion to treat the headache comprises discharging the primary anesthetic through a wicking material.

12. A method of treating a headache comprising:

priming a patient's nasal cavity with a first dose of anesthetic; and subsequently discharging a main anesthetic proximate to the sphenopalatine ganglion.

13. The method of claim 12 wherein discharging a main anesthetic proximate to the sphenopalatine ganglion comprises discharging a main anesthetic through a flexible nozzle inserted into the patient's nasal cavity.

* * * * *